United States Patent
Birdsley et al.

(10) Patent No.: US 7,019,511 B1
(45) Date of Patent: Mar. 28, 2006

(54) OPTICAL ANALYSIS OF INTEGRATED CIRCUITS

(75) Inventors: Jeffrey D. Birdsley, Austin, TX (US);
Michael R. Bruce, Austin, TX (US);
Brennan V. Davis, Austin, TX (US);
Rosalinda M. Ring, Austin, TX (US);
Daniel L. Stone, Cedar Park, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 733 days.

(21) Appl. No.: 09/755,008

(22) Filed: Jan. 5, 2001

(51) Int. Cl.
*G01J 5/02* (2006.01)
*G01R 31/00* (2006.01)
*G01R 31/302* (2006.01)

(52) U.S. Cl. .................... 324/96; 324/750; 324/753; 324/501; 250/341.4

(58) Field of Classification Search .............. 324/96
See application file for complete search history.

(56) References Cited

U.S. PATENT DOCUMENTS

| | | | | |
|---|---|---|---|---|
| 5,381,421 A | * | 1/1995 | Dickol et al. | 714/744 |
| 5,999,006 A | * | 12/1999 | Kikuchi | 324/750 |
| 6,072,179 A | * | 6/2000 | Paniccia et al. | 250/341.4 |

* cited by examiner

*Primary Examiner*—Fahmy Wael
*Assistant Examiner*—Shrinivas H. Rao
(74) *Attorney, Agent, or Firm*—Crawford Maunu PLLC

(57) ABSTRACT

The invention is directed to a system and method for analyzing an integrated circuit having silicon on insulator (SOI) structure. According to one example embodiment of the present invention, an optical beam arrangement is adapted to direct a modulated beam at a selected portion of the integrated circuit. The beam is sufficiently modulated to inhibit optical beam intrusion on the structure and operation of the integrated circuit. A reflected optical waveform response is obtained from the SOI selected portion. The inhibition of optical beam intrusion enhances the ability to analyze integrated circuits using an optical beam, making possible the use of analysis methods that otherwise would be difficult or even impossible to use.

9 Claims, 3 Drawing Sheets

OPTICAL ANALYSIS OF INTEGRATED CIRCUITS

FIELD OF THE INVENTION

The present invention relates generally to semiconductor devices and their fabrication and, more particularly, to semiconductor devices and their manufacture involving techniques for analyzing and debugging circuitry within an integrated circuit.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such high-density and high functionality in semiconductor devices has been the demand for increased numbers of external electrical connections to be present on the exterior of the die and on the exterior of the semiconductor packages which receive the die, for connecting the packaged device to external systems, such as a printed circuit board.

As the manufacturing processes for semiconductor devices and integrated circuits increase in difficulty, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured.

To increase the number of pad sites available for a die, different chip packaging techniques have been used. One technique is referred to as a dual in-line package (DIP) in which bonding pads are along the periphery of the device. Another technique, called controlled-collapse chip connection or flip chip packaging, uses the bonding pads and metal (solder) bumps. The bonding pads need not be on the periphery of the die and hence are moved to the site nearest the transistors and other circuit devices formed in the die. As a result, the electrical path to the pad is shorter. Electrical connections to the package are made when the die is flipped over the package with corresponding bonding pads. Each bump connects to a corresponding package inner lead. The resulting packages have a lower profile and have lower electrical resistance and a shortened electrical path. The output terminals of the package may be ball-shaped conductive-bump contacts (usually solder or other similar conductive material) and are typically disposed in a rectangular array. These packages are occasionally referred to as "Ball Grid Array" (BGA). Alternatively, the output terminals of the package may be pins, and such a package is commonly known as the pin grid array (PGA) package.

For BGA, PGA and other types of packages, once the die is attached to the package, the backside portion of the die remains exposed. The transistors and other circuitry are generally formed in a very thin epitaxially grown silicon layer on a single crystal silicon wafer of which the die is singulated from. In a structural variation, a layer of insulating silicon dioxide is formed on one surface of a single crystal silicon wafer followed by the thin epitaxially grown silicon layer containing the transistors and other circuitry. This wafer structure is termed "silicon on insulator" (SOI) and the silicon dioxide layer is called the buried oxide layer (BOX). The epitaxial silicon layer is typically about 10 micrometers thick, the buried oxide layer less than about 1 micrometer, and the bulk silicon greater than 500 micrometers. The transistors formed on the SOI structure show decreased drain capacitance, resulting in a faster switch transistor.

The side of the die including the epitaxial layer containing the transistors and the other active circuitry is often referred to as the circuit side of the die or front side of the die. The circuit side of the die is positioned very near the package. The circuit side opposes the backside of the die. Between the backside and the circuit side of the die is single crystalline silicon and, in the case of SOI circuits, also a buried oxide layer. The positioning of the circuit side provides many of the advantages of the flip chip.

Post manufacture analysis of SOI flip chip dies having a buried oxide layer (BOX) typically is destructive for various reasons, such as a need to remove substrate from the flip chip back side in order to access the circuitry. When too much substrate is removed, or when the removal process is not adequately controlled, the circuitry in the die can be damaged. Optical beam probing of circuitry is one analysis method that is used to analyze a semiconductor die through the substrate. However, intrusion of the optical beam into the SOI circuitry can result in disruption of the operation of, or even damage to, circuitry components. Thus, there is an unmet need for methods of analyzing flips chip BOX die circuit operation without excessively disrupting the die.

SUMMARY OF THE INVENTION

The present invention is directed to a method and system for optical beam analysis of a semiconductor device having SOI structure. The present invention is exemplified in a number of implementations and applications, some of which are summarized below.

According to an example embodiment of the present invention, a modulated optical beam is directed at a selected portion of an integrated circuit having silicon on insulator (SOI) structure. The modulation of the beam is selected to sufficiently inhibit intrusion of the beam upon the integrated circuit. A reflected optical waveform response is obtained therefrom for use in analyzing the device. In this manner, analysis of an integrated circuit having SOI structure is achieved without necessarily destroying or modifying the integrated circuit structure.

In a more particular example embodiment of the present invention, a SOI integrated circuit die having a circuit side opposite a back side is placed in an analysis arrangement. An infrared laser is arranged to direct a laser beam into the back side and to a selected portion in the die. The laser is pulsed at intervals having a duration of about 100 femto-seconds, the interval being selected to sufficiently inhibit intrusion of the laser upon the die. The die is operated and a waveform is obtained as a function of the operation of the die and a reflection of the optical beam. The waveform is then used for die analysis, such as troubleshooting, defect detection, quality assurance or design testing.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
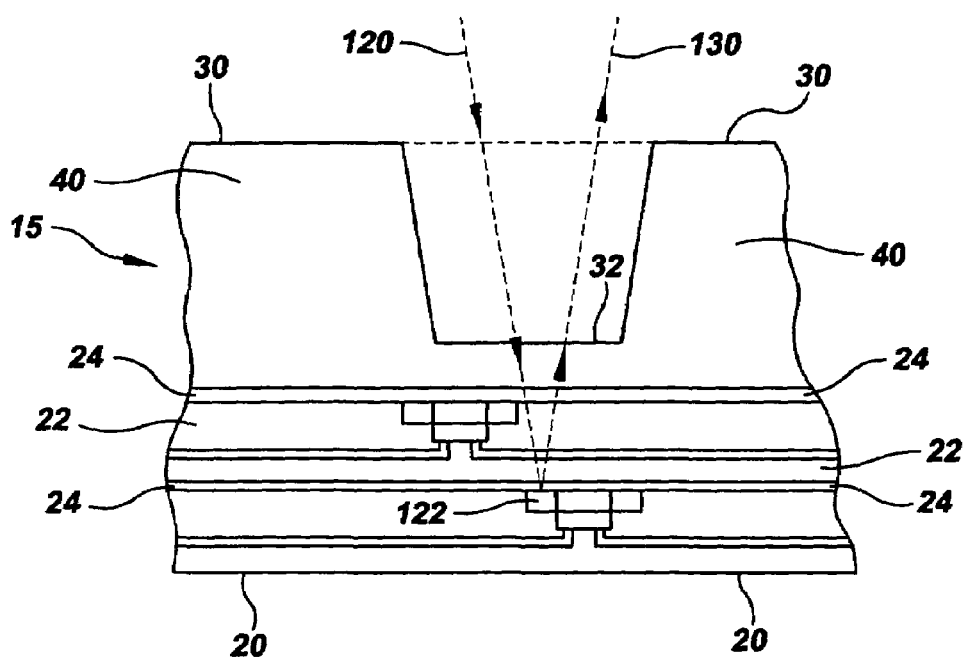
FIG. 1 illustrates a SOI flip chip undergoing analysis, according to an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable for a variety of different types of semiconductor devices, and the invention has been found to be particularly suited for analyzing silicon on insulator (SOI) integrated circuit dies. While the present invention is not necessarily limited to such SOI devices, various aspects of the invention may be appreciated through a discussion of various examples using this context.

According to an example embodiment of the present invention, an optical beam is directed at a selected portion of a conventional flip chip type SOI die. The beam is pulsed at an interval that is sufficient to inhibit intrusion of the beam into the die. A reflected optical response from the SOI is obtained from the die and used to generate a waveform representing an electrical characteristic of the die. In this manner, analysis of SOI flip chip dies is made possible while maintaining minimal beam intrusion, and without necessarily destroying the die.

According to a more particular example embodiment of the present invention, enough substrate is removed from a back side of an SOI die to facilitate penetration of an infrared laser beam to a selected portion within the die. Once the substrate has been removed, an infrared laser beam is directed at the back side of the die. The beam is focused at a circuitry node of interest located at a specific depth within a circuitry layer of the die. The beam is pulsed at a duration in the femto-second-range (e.g., about 100 femto-seconds long), and the pulsed beam passes through the back side to the node. A reflected beam response is obtained from the node of interest, and characteristics of the reflection are used to generate a voltage waveform that is used to analyze the die. The femto-second pulse duration aids in analysis of circuitry operating at high frequency, and in circuitry located such that analysis using a laser having a longer pulse or constant application would harm the die. Once the waveform is obtained, analysis may include comparing the waveform response obtained from the die with responses from defective or non-defective integrated circuit dies of similar structure and configuration.

In another example embodiment of the present invention, FIG. 1 shows a SOI die 15 with a modulated laser beam 120 directed at a circuitry node 122 of interest located at a specific depth in the circuitry layer. The beam passes through a back side 30 of the die to the node 122 and reflects as beam 130 that can be used to analyze the die circuitry. The laser beam 120 is modulated in a manner that makes possible the detection of a response from the node 122 without adversely affecting surrounding circuitry and interconnects. In addition, the laser modulation is particularly useful for analyzing dies having circuitry located in close proximity and for accessing circuitry located below another circuit layer, as shown in FIG. 1.

The die can be prepared in various manners for analysis. According to an example embodiment of the present invention, the die is thinned prior to analysis. In one implementation, the back side is globally thinned and the beam 120 is directed through the globally thinned surface, such as shown by dashed lines in FIG. 1. Mechanical polishing is one method for global thinning. In another implementation, the die 15 receives two or three steps of thinning in the process. After the die is globally thinned, local thinning techniques, such as laser microchemical etching, are then used to thin the silicon in an area to a level that is thinner than the die size as shown by exposed region 32. One method for laser microchemical etching of silicon is focusing a laser beam on the backside of the silicon surface to cause local melting of silicon in the presence of chlorine gas. The molten silicon reacts very rapidly with chlorine and forms silicon tetrachloride gas, which leaves the molten (reaction) zone. After substrate removal, the thinned die 15 is analyzed as described herein.

Figure 2:
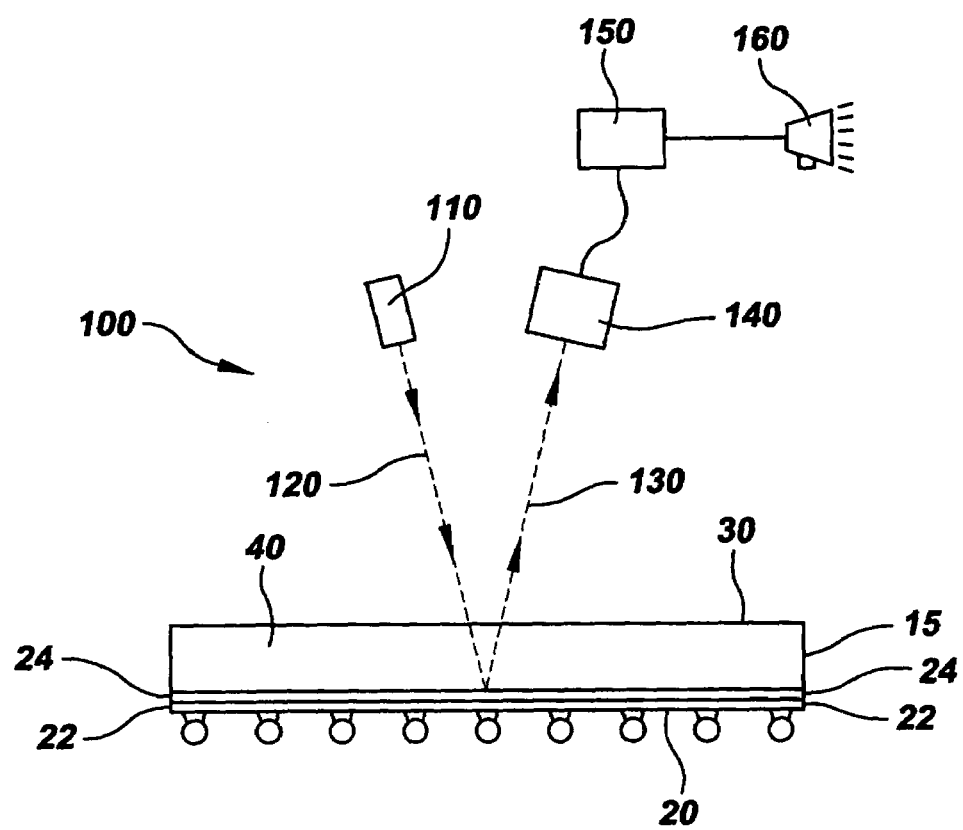
FIG. 2 illustrates a SOI flip chip undergoing analysis, according to another example embodiment of the present invention.

FIG. 2 shows a side view of a SOI die 15 having a circuit side 20 and a backside 30 undergoing analysis according to an example embodiment of the invention. A system 100 is adapted to obtain non-contact optical waveform responses from devices and structures in the die 15. An optical beam arrangement 110, such as a laser, generates a modulated beam 120 and is arranged to direct the beam at the backside 30 of the SOI die 15. The beam 120 passes through a portion of the SOI die and reflects from a node in an epitaxial layer 22, resulting in reflected beam 130. Arrangement 140 detects the reflected beam 130 in a manner that makes possible analysis of the die 15 therefrom.

In a more particular example embodiment of the present invention, the beam arrangement 110 is adapted to generate an infrared laser beam that is pulsed at a duration in the femto-second ($10^{-15}$) range. A femto-second laser suitable for use in connection with the present invention is the titanium:saphire laser commercially available from a number of sources, including CDP Laser and Scanning Systems of Moscow, Russia. The beam is focused on the node at a selected depth in the exptaxial layer 22. The focused nature of the laser beam 120 allows the system 100 to pinpoint a specific circuitry node in the epitaxial layer structure 22. The short laser pulse duration imposes a minimal intrusion on the area of interest of the SOI flip chip 15, and the infrared beam 120 limits the energy impinging on the die 15. The depth focusing ability, coupled with the minimal intrusion upon the die 15, is useful in dies of complex circuitry containing multiple stacked layers of components.

In another implementation, the system 100 is further adapted to stimulate the die circuitry, and obtains optical waveforms from the reflected laser beam 130 that are responsive to the stimulus. The stimulation may include, for example, applying a test vector pattern including a series of voltage inputs to the circuit that cause the die to operate under normal or failure conditions. In addition, the stimulation can be applied in a loop that cycles the circuit through one or more failure conditions. The system 100 then obtains a response from the circuit receiving the stimulus.

In another example embodiment of the present invention, a computer arrangement 150 is coupled to the detection arrangement 140. The computer arrangement 150 is adapted to receive and process the reflected optical waveform response 130 collected by the detection arrangement 140. A visual output arrangement 160 may be coupled to the computer arrangement 150 and adapted to present data from the computer arrangement 150 for visual analysis. The visual output arrangement 160 may include a video monitor and a printer. The computer arrangement 150 may also include waveform analysis software for further analysis of the reflected modulated optical waveform response 130 collected by the detection arrangement 140.

Figure 3:
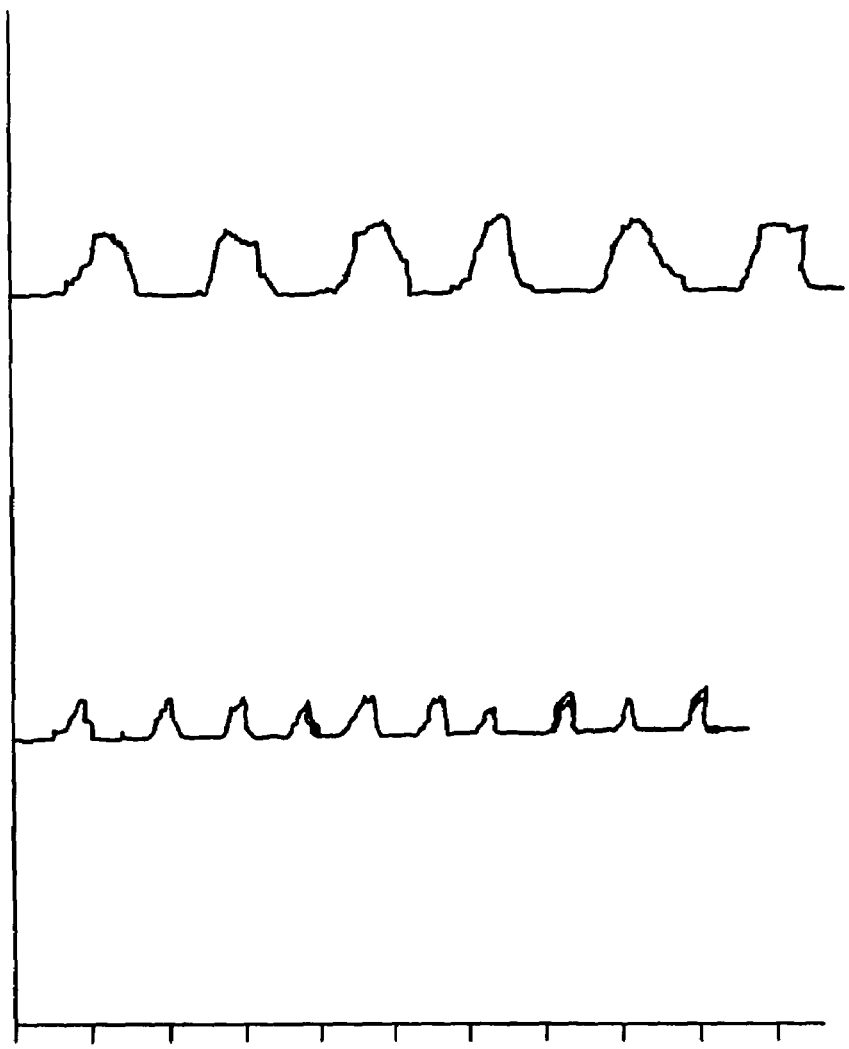
FIG. 3 is a graphic representation of waveforms acquired from a SOI flip chip die, according to another example embodiment of the present invention.

Example responses include voltage waveforms acquired from the system detector 140, such as shown in FIG. 3. Voltage waveforms such as that shown in FIG. 3 can be used to detect a defect or verify performance of an integrate circuit die in various manners. For instance, the voltage waveform can be compared to a reference waveform from a die known to exhibit a defect for which the die being analyzed is suspected to have. The waveform can also be compared to that of a die that is known to be non-defective. Variations in the waveform can then be used to detect a defect.

While the present invention has been described with reference to several particular example embodiments, those skilled in the art will recognize that many changes may be made thereto without departing from the spirit and scope of the present invention, which is set forth in the following claim.

What is claimed is:

1. An arrangement for analyzing an integrated circuit having a silicon on insulator (SOI) structure, the arrangement comprising;
   means for directing a modulated optical beam at a selected portion of the SOI structure, the modulation being adapted to inhibit optical beam intrusion upon the integrated circuit; and
   means for obtaining a reflected optical waveform response from the SOI selected portion.

2. A system for analyzing an integrated circuit having a silicon on insulator (SOI) structure, the system comprising;
   an optical beam arrangement adapted to direct a modulated optical beam at a selected portion of the SOI structure and to inhibit intrusion of the optical beam upon the integrated circuit via the modulation; and
   a detection arrangement adapted to detect a reflected optical waveform response from the SOI structure selected portion.

3. The system for analyzing an integrated circuit having a silicon on insulator (SOI) structure of claim 2, wherein the optical beam arrangement includes an infrared laser.

4. The system for analyzing an integrated circuit having a silicon on insulator (SOI) structure of claim 3, wherein the optical beam arrangement is adapted to pulse the laser at femto-second-range pulses.

5. The system for analyzing an integrated circuit having a silicon on insulator (SOI) structure of claim 3, further comprising a testing device adapted to operate the die.

6. The system for analyzing an integrated circuit having a silicon on insulator (SOI) structure of claim 2, further comprising a computer arrangement coupled to the detector arrangement and adapted to receive and process the reflected optical waveform response.

7. The system for analyzing an integrated circuit having a silicon on insulator (SOI) structure of claim 6, further comprising a visual output arrangement coupled to the computer arrangement and adapted to present data from the computer arrangement for visual analysis.

8. The system for analyzing an integrated circuit having a silicon on insulator (SOI) structure of claim 7, wherein the visual output arrangement includes at least one of: a video monitor and a printer.

9. The system for analyzing an integrated circuit having a silicon on insulator (SOI) structure of claim 8, wherein the computer arrangement includes waveform analysis software.

* * * * *